United States Patent [19]

Nafis et al.

[11] Patent Number: 5,740,802
[45] Date of Patent: Apr. 21, 1998

[54] COMPUTER GRAPHIC AND LIVE VIDEO SYSTEM FOR ENHANCING VISUALIZATION OF BODY STRUCTURES DURING SURGERY

[75] Inventors: Christopher Allen Nafis, Rexford; Timothy Patrick Kelliher, Nassau; William Edward Lorensen, Ballston Lake; Harvey Ellis Cline, Schenectady, all of N.Y.; David Egidio Altobelli, Wilmington; Ron Kikinis, Brookline, both of Mass.; Robert David Darrow, Scotia; Charles Lucian Dumoulin, Ballston Lake, both of N.Y.

[73] Assignee: General Electric Company, Schenectady, N.Y.

[21] Appl. No.: 569,560

[22] Filed: Dec. 8, 1995

Related U.S. Application Data

[63] Continuation of Ser. No. 342,690, Nov. 21, 1994, abandoned, which is a continuation of Ser. No. 49,913, Apr. 20, 1993, abandoned.

[51] Int. Cl.⁶ .................................................. A61B 5/05
[52] U.S. Cl. ........................ 128/653.1; 369/78; 439/26.7; 352/60
[58] Field of Search ................ 128/653.1; 364/413.01, 364/413.02, 413.13, 413.22, 578; 358/448, 450; 359/458; 353/7; 352/60–63; 434/262, 267; 606/130

[56] References Cited

U.S. PATENT DOCUMENTS

| | | | |
|---|---|---|---|
| 4,395,731 | 7/1983 | Schoolman | 358/88 |
| 4,719,585 | 1/1988 | Cline et al. | |
| 4,722,056 | 1/1988 | Roberts et al. | 364/413.22 |
| 4,985,834 | 1/1991 | Cline et al. | |
| 5,039,198 | 8/1991 | Van Beek | 385/117 |
| 5,099,846 | 3/1992 | Hardy | 128/653.1 |
| 5,187,658 | 2/1993 | Cline et al. | |
| 5,222,477 | 6/1993 | Lia | 128/6 |
| 5,255,211 | 10/1993 | Redmond | 364/578 |
| 5,261,404 | 11/1993 | Mick et al. | 128/653.1 |
| 5,603,318 | 2/1997 | Heilbrun et al. | 128/653.1 |

OTHER PUBLICATIONS

*Computer Graphics World*, Jul. 1994, "Scientific and medical applications of Virtual Reality . . . ", Mahoney, pp. 20–26.

*Proceedings of the SPIE — The International Society fir Optical Eng.*, vol. 1083, pp. 42–52, 1989, Chung et al., "Exploring Virtual Worlds with Head–Mounted Displays".

*IEEE Engineering in Medicine and Biology Magazine*, Mar. 1992, Beltrame et al., "Integrated Imaging for Neurosurgery", pp. 51–66.

*Computer Vision and Pattern Recognition*, 1994, cat No. 1063–6919/94, Grimson et al., "An Automatic Registration Method for Frameless Stereotaxy, Image Guided Surgery, and Enhanced Reality Visualization", pp. 430–436.

*IEEE Colloq. (1991), No. 083: 3D Imaging Techniques for Medicine,* Hill et al., "3D synergistic imaging as an aid to image interpretation and surgical planning", three pages.

(List continued on next page.)

Primary Examiner—Brian L. Casler
Attorney, Agent, or Firm—Lawrence P. Zale; Marvin Snyder

[57] ABSTRACT

An interactive surgery planning and display system mixes live video of external surfaces of the patient with interactive computer generated models of internal anatomy obtained from medical diagnostic imaging data of the patient. The computer images and the live video are coordinated and displayed to a surgeon in real-time during surgery allowing the surgeon to view internal and external structures and the relation between them simultaneously, and adjust his surgery accordingly. In an alternative embodiment, a normal anatomical model is also displayed as a guide in reconstructive surgery. Another embodiment employs three-dimensional viewing.

14 Claims, 7 Drawing Sheets

OTHER PUBLICATIONS

*Computer–Based Medical Systems, 1992 IEEE Symposium,* Hemler et al., "A Three Dimensional Guidance System for Frameless Stereotactic Neurosurgery", pp. 309–314, cat. No. 0–8186–2742–5/92.

*Proceedings of the SPIE,* vol. 1083, pp. 42–52, 1989, Chung et al., "Exploring Virtual Worlds with Head–Mounted Displays" (Abstract provided only).

"A Frameless Stereotaxic Operating Microscope for Neurosurgery" by E. M. Friets, J. W. Strohbehn, J. F. Hatch, and D. W. Roberts, IEEE Transactions on Biomedical Engineering, vol. 36., No. 6, pp. 608–617, Jun. 1989.

"The Flock of Birds Installation and Operation Guide", Ascension Technology Corporation, Jul. 5, 1992.

"Interactive Stereotactic Surgical System for the Removal of Intracranial Tumors Utilizing the $CO_2$ Laser and CT–Derived Database" by B. A. Kall, P. J. Kelly, and S. J. Goerss, IEEE Transactions on Biomedical Engineering, vol. BME–32, No. 2, pp. 112–116, 1985.

"Comprehensive Computer–Assisted Data Collection Treatment Planning and Interactive Surgery" by B. A. Kall, P. J. Kelly, and S. J. Goerss, Medical Imaging, vol. 767 pp. 509–514, 1987.

"Video Toaster System 2.0 Software Manual" 1992 by J. M. Herbert, NewTek Inc.

"Portable, Low Cost Devices for Videotaping, Editing and Displaying Field Sequential Stereoscopic Motion Pictures and Video" by M. Starks, Stereoscopic Displays and Applications Proc. SPIE vol. 1256, pp. 266–271, 1990.

U.S. Patent application Ser. No. 07/631,121 filed Dec. 20, 1990 (RD–20,348) "Segmentation of Stationary and Vascular Surfaces in Magnetic Resonance Imaging" by Harvey E. Cline, Steven P. Souza and William E. Lorensen.

U.S. Patent Application, Ser. No. 07/812,479 filed Dec. 23, 1991 (Docket No. RD–21,335) "Solid Model Generation by Span Method Using Dividing Cubes" by Harvey E. Cline, William E. Lorensen and Siewalt Ludke.

Wall Street Journal "Science" column, Mar. 3, 1993.

"Intraoperative Navigation in Craniomaxillofacial Surgery" D. E. Altobelli, R. Kikinis, J. B. Mulliken, W. E. Lorensen, H. Cline, F. Jolesz, Journal of Oral and Maxillofacial Surgery, vol. 49, No. 8, Supp. 1, Aug. 1991 — abstract of the oral presentation at AAOMS Sep. 25, 1991.

A filming was performed on Apr. 21, 1993 for "Beyond 2000" on the Cable TV Discovery Channel (DSC) to be aired sometime later.

"3D Ultrasound Display Using Optical Tracking", Peter H. Mills, Henry Fuchs, Proceedings of the First Conf. on Visualization in Biomedical Computer, IEEE Computer Soc.Press, USA, 22 May 1990, pp. 490–497.

"The DSI Technique Used on DDD Paced Patients", J. Snoeck, M. Berkhof, C. Vrints, M. Claeys, H. Decoster, M. Roovers, H. Heuten, Proceedings of Computers in Cardiology, IEEE Computer Soc. Press, USA, 23 Sep. 1991 — pp. 509–512.

"Computer Assisted Planning for Craniofacial Surgery", D.E. Altobelli, Proceedings of the 12th Annual Conf. and Expo. dedicated to Computer Graphics, USA, 22 Apr. 1991, pp. 162–166.

COMPUTER GRAPHIC AND LIVE VIDEO SYSTEM FOR ENHANCING VISUALIZATION OF BODY STRUCTURES DURING SURGERY

This application is a continuation of application Ser. No. 08/342,690 filed Nov. 21, 1994 now abandoned, which is a continuation of application Ser. No. 08/049,913 filed Apr. 20, 1993, now abandoned.

CROSS REFERENCE TO RELATED APPLICATIONS

This application is related to applications "System For Displaying Solid Cuts For Surfaces of Solid Models" by William E. Lorensen, Harvey E. Cline, Bruce Teeter, and Siegwalt Ludke, Ser. No. 07/812,394, "Solid Models Generation By Span Method Using Dividing Cubes", by Harvey E. Cline, William E. Lorensen and Siegwalt Ludke, Ser. No. 07/812,479, and "Apparatus and Method For Displaying Surgical Cuts in Three-Dimensional Models" by Harvey E. Cline, William E. Lorensen and Siegwalt Ludke, Ser. No. 07/812,395, all filed Dec. 23, 1991, and all assigned to the present assignee.

BACKGROUND OF THE INVENTION

1. Field of the Invention

The present invention relates to a system for aiding a surgeon in visualizing body structures during surgery and more specifically to a system which displays, in real time, interactive images of both internal and external body structures to aid in surgery.

2. Discussion of Prior Art

Presently, during surgery, surgeons view several static views of the patient in the operating room. Typically these are transparencies of magnetic resonance (MR), computed tomography (CT), or ultrasound images. Since these images are two dimensional static images, the surgeons must determine actual three-dimensional (3D) location and shape of desired internal structures within the patient from the 2D images which they are viewing. Conceptually, the surgeon constructs a 3D model of the internal structures and correlates these internal structures with visible external structures of the patient where they must cut. This is often difficult because the scale and the orientation of the 2D image may differ from what the surgeon is seeing, and the surgeon may not be able to view both the patient and the medical diagnostic images simultaneously.

Another technique employed in localization of internal structures during surgery is known as stereotactic surgery as described in "Interactive Stereotactic Surgical System for the Removal of Intracranial Tumors Utilizing the $CO_2$ Laser and CT-Derived Database" by B. A. Kall, P. J. Kelly, and S. J. Goerss, IEEE Transactions on Biomedical Engineering, vol. BME-32, no. 2, pp 112–116, 1985; and "Comprehensive Computer-Assisted Data Collection Treatment Planning and Interactive Surgery" by B. A. Kall, P. J Kelly, and S. J. Goerss, Medical Imaging, vol. 767 pp. 509–514, 1987. With this approach, a rigid mechanical frame is attached to the patient before a CT or MR procedure. The frame and its landmarks can be seen in the resulting images. Mechanisms on the frame position a probe at specific location within the image. The disadvantages of this approach are that the frame limits access to the patient, and the images are static images which do not follow the patient if he moves during surgery.

A third technique used for localization of internal structures is described in "A Frameless Stereotaxic Operating Microscope for Neurosurgery" by E. M. Friets, J. W. Strohbehn, J. F. Hatch, and D. W. Roberts, IEEE Transactions on Biomedical Engineering, vol. 36., no. 6, pp 608–617, June 1989.

Three dimensional models of anatomy can be created from data of different medical imaging modalities as described in the application listed above in the "CROSS REFERENCE TO RELATED APPLICATIONS". These applications describe creating and manipulating models of internal structures of patients and providing images of selected structures at desired orientations to an operator. These allow visualization of internal structures as solid models.

Currently there is a need for a system to aid surgeons in surgery which interactively displays computer generated models of internal structures in correct relation with external structures of the patient to guide during surgery.

OBJECTS OF THE INVENTION

An object of the present invention is to provide a system which aides in surgery by interactively displaying an image of external structures superimposed upon internal structures, even if the patient changes his position.

Another object of the present invention is to provide an interactive system which displays desired external and internal structure, both having the same scale and viewed from the same orientation angles.

Another object of the present invention is to provide a guide image of normal anatomy superimposed on body structures of a patient to aid surgeons in performing reconstructive surgery.

SUMMARY OF THE INVENTION

A real-time surgery apparatus for displaying interactive internal and external images of a patient employs a video camera for providing real-time images of exposed surfaces of the patient.

A medical imaging device obtains three-dimensional (3D) imaging data of internal structures of said patient which are fed to a workstation. The workstation creates three-dimensional (3D) computer generated models which may be manipulated without further need for the medical imaging device. Computer generated images of the models are interactively oriented and scaled to coincide with the real-time video images.

A video mixer mixes portions of the computer generated image and the live video to display external structures of the patient superimposed over the computer generated images of internal structures in their correct relationship.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
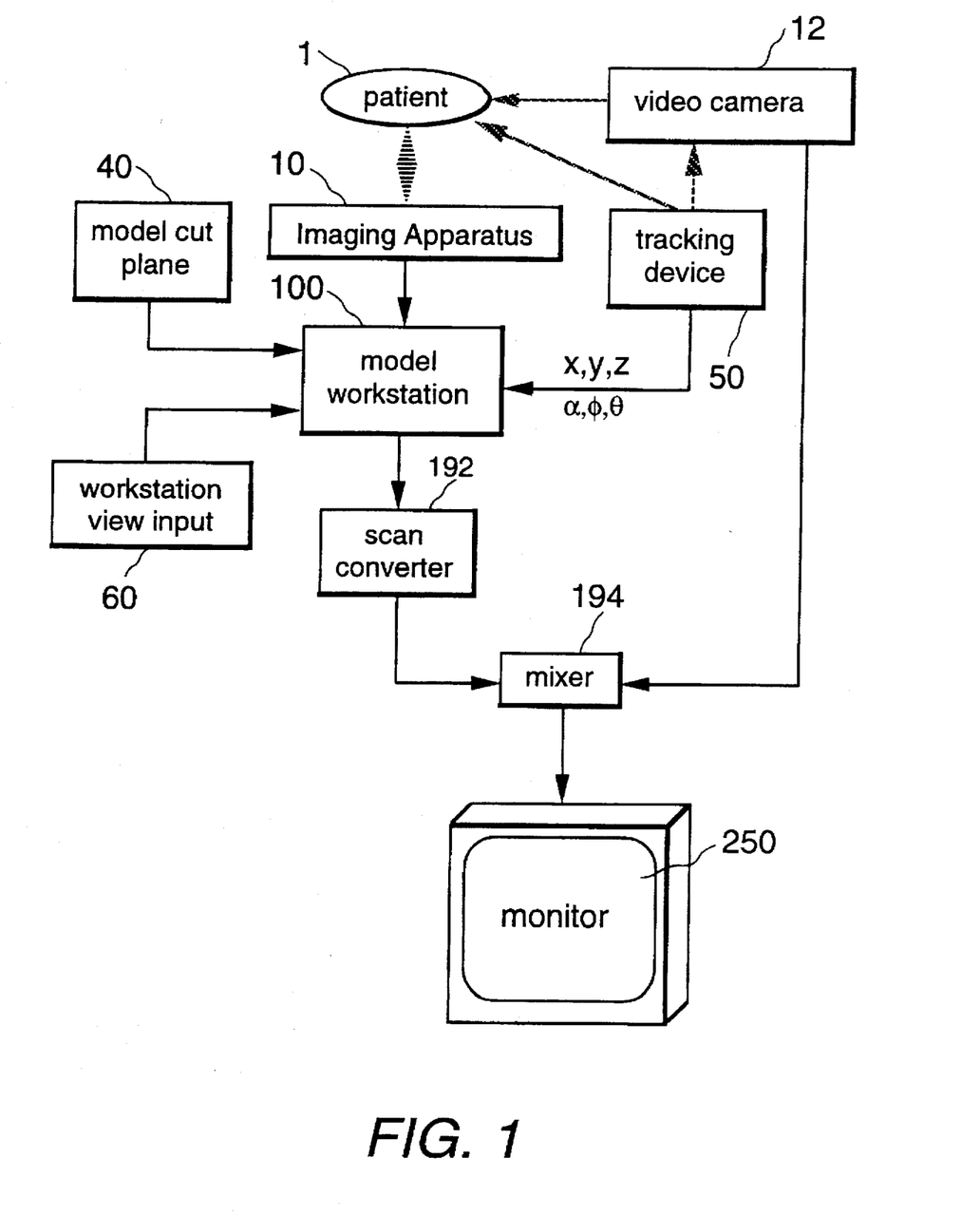
FIG. 1 is a simplified block diagram of a first embodiment of a surgical apparatus according to the present invention.

In FIG. 1, a patient 1 on which surgery is to be performed, is scanned by a medical imaging apparatus such as a magnetic resonance (MR) imaging apparatus, a computed axial tomography (CAT) apparatus, a positron emission tomography (PET) or similar imaging device capable of creating volumetric data, or 3-dimensional (3-D) data, from internal structures of the patient. After imaging, apparatus 10 provides the volumetric data to a model workstation 100. Once the volumetric data has been provided to model workstation 100, there is no further need for imaging apparatus 10. This is important since it does not require surgery to then be planned and performed with the patient situated within the confines of an imaging apparatus, which is very constricting in the case of MR imaging. Model workstation 100 stores the volumetric data and creates computer generated models from the data capable of being scaled, rotated and otherwise manipulated, without the further need for imaging apparatus 10.

An imaging device capable of sensing external structures, such as a live video camera 12, monitors patient 1. A tracking device 50 coupled to both video camera 12 and patient 1 determines a relative roll $\alpha$, pitch $\theta$, and yaw $\phi$ orientation between video camera 12 and subject 1. Tracking device 50 may be a 6-degrees of freedom tracking device as described in "The Flock of Birds" Installation and Operation Guide, Ascension Technology Corporation, Jul. 5, 1992. Tracking device 50 also determines a location (in Cartesian coordinates) of video camera 12 with relation to patient 1. Patient 1 is assumed to be at the origin of the Cartesian coordinate system (x,y,z)=(0,0,0), therefore all distances relative to the patient are simply the (x,y,z) location. The location and orientation are interactively provided to model workstation 100 by tracking device 50. The location and orientation may also be provided manually to model workstation(s) in different embodiments.

Model workstation 100 processes the three-dimensional (3D) volumetric data it receives and determines surfaces between differing types of tissue. Connectivity of similar types of tissue adjacent to one another is then determined. This is known as segmentation. When the 3-D volumetric data has been segmented into internal structures, each internal structure may be treated as a separate solid object by model workstation 100. The model workstation has the capability of selectively displaying desired internal structures, color coding structures and severing, rotating and translating internal structures in order to manipulate the internal structures in a desired manner to provide visualization to an operator working model workstation 100.

Model workstation 100 receives input data from a model cut plane input device 40 and a workstation view input device 60 to select the method of displaying internal structures of patient 1. Tracking device 50 provides relative orientation data between video camera 12 and patient 1 and scaling, which allows model workstation 100 to synthesize an interactive computer generated image of internal structures of patient 1 and have it coincide with the real-time image from video camera 12. This interactive computer generated image is converted from a computer monitor signal, such as an RGB computer monitor signal, to a video format as it is passed through a scan converter 192. The computer generated image, in video format, is provided to a video mixer 194. A real-time video signal from video camera 12 is also passed to video mixer 194. Video mixer 194 provides a desired mixture of the video signal from the video camera 12 with the computer generated image originally from model workstation 100. Video mixer 194 may receive input signals from the operator, for example, through a workstation view input 60. This may involve the degree of transparency of each image, or any of various other special effects. One very useful special effect is a movable window which has 0% transparency (100% opaqueness) superimposed upon another image. When the window image is of internal structures superimposed upon external structures, it creates the illusion of external structures cut away within the window, exposing underlying internal structures. Other video special effects such as a "50/50 mix" and a "side to side wipe" described in "Video Toaster System 2.0 Software Manual" 1992 by J. M. Herbert, NewTek Inc. may also be employed. Video mixer 194 provides real-time video signal from video camera 12 and the computer generated image of internal structures to a monitor 250, allowing both internal and external structures to be visible simultaneously. The resulting image displayed on monitor 250 provides an interactive real-time image of patient, even if the patient moves during surgery. Since internal structures and their relation to exposed external structures are simultaneously displayed, the surgeon perceives a very accurate indication of where he should cut through external structures to arrive at a desired internal structure while avoiding vital internal structures.

Figure 2:
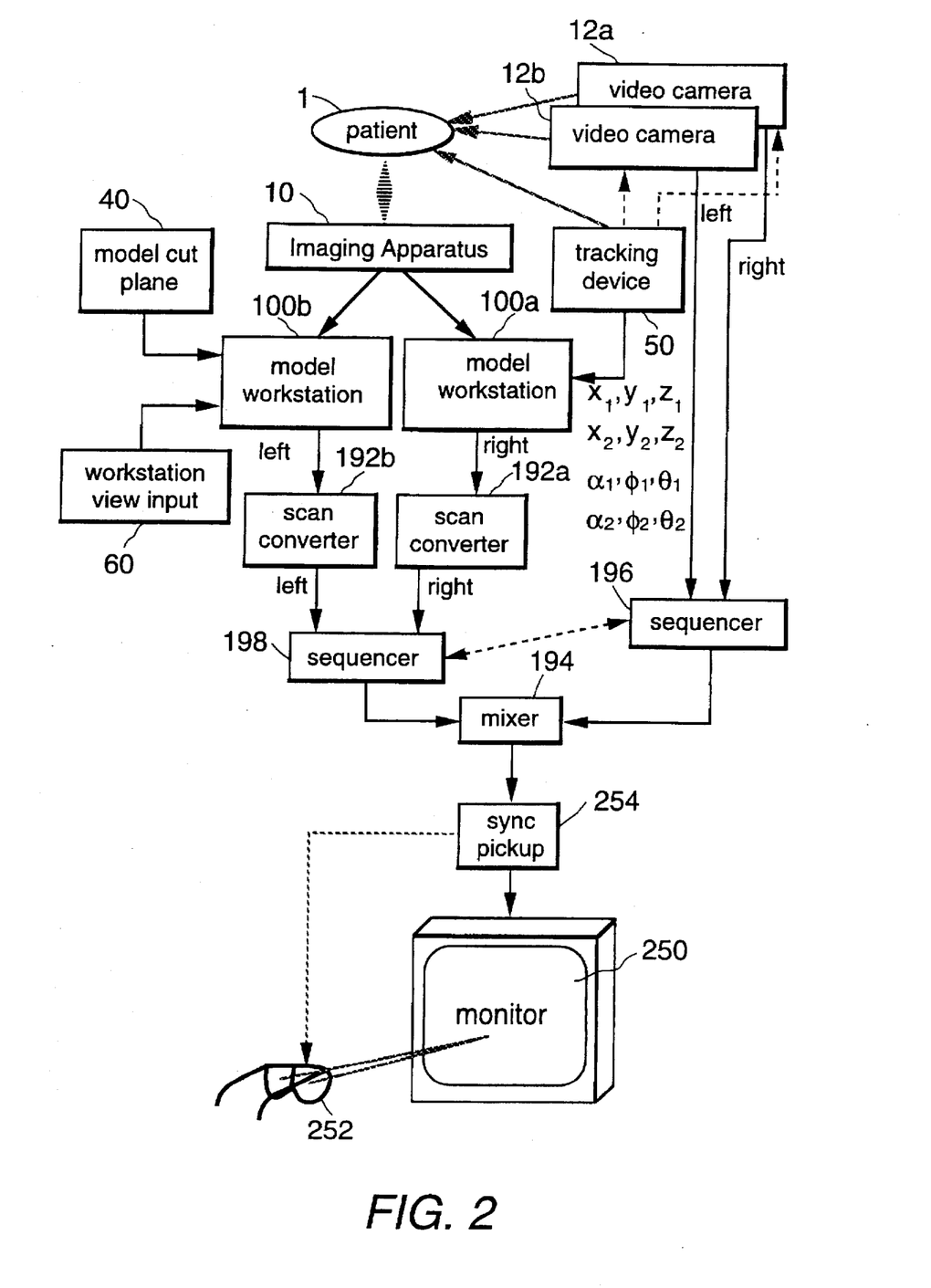
FIG. 2 is a simplified block diagram of a second embodiment of a surgical apparatus according to the present invention.

FIG. 2 illustrates an alternative embodiment of the present invention in which a pair of video cameras 12a, 12b create a real-time video image of external structures of patient 1. Video cameras 12a, 12b differ in their orientation with relation to the patient to simulate a stereoscopic view with video camera 12a corresponding to a right view from an operator's right eye, and video camera 12b corresponding to a left view from an operator's left eye. Video cameras 12a and 12b together provide a stereoscopic view of external structures of patient 1. Tracking device 50 also tracks the relative location $(x_1,y_1,z_1)$ and orientation angle $(\alpha_1,\phi_1,\theta_1)$ between video camera 12a and patient 1. Tracking device 50 tracks a second location $(x_2,y_2,z_2)$ and orientation $(\alpha_2,\phi_2,\theta_2)$ between video camera 12b and patient 1. The locations and orientations are fed to model workstation 100a, 100b which create a right and left computer graphic image at locations $(x_1,y_1,z_1)$, $(x_2,y_2,z_2)$, respectively, and orientations $(\alpha_1,\phi_1,\theta_1)$ $(\alpha_2,\phi_2,\theta_2)$, respectively, corresponding to the views of video cameras 12a, 12b, respectively.

Video cameras 12a and 12b each pass a real-time video signal to a sequencer 196 which selects a signal from one of the two video cameras and passes it to mixer 194, then selects the signal from the other camera and passes it to mixer 194. Sequencer 196 alternates between the video signal from video cameras 12a, 12b in a regular fashion several times per second, for example 30 times per second, so that each video signal is provided at ½ the video frame rate.

Model workstations 100a, 100b pass a left and right computer generated image, respectively, pertaining to a left and right view, respectively, to scan convertors 192a, 192b, respectively which convert the computer generated image signals to video format, and pass the converted computer generated signals to a sequencer 198. Sequencers 196 and 198 may be conventional video sequencers as described in "Portable, Low Cost Devices for Videotaping, Editing and Displaying Field Sequential Stereoscopic Motion Pictures and Video" by M. Starks, Stereoscopic Displays and Applications Proc. SPIE Vol. 1256, pp. 266–271, 1990.

Sequencer 198 passes the left computer generated image to video mixer 194 at the same time sequencer 196 passes the video signal corresponding to the left view to video mixer 194. Sequencer 196 then passes the video image from camera 12a corresponding to the right view to mixer 194 at the same time that sequencer 198 passes the right computer generated image to mixer 194. Sequencers 196 and 198 alternate many times per second, in synchronization, between right and left views. Video mixer 194 mixes portions of the signals it receives and displays them on a monitor 250.

The image on monitor 250 is time multiplexed to produce an image to the left eye and right eye of the operator in an alternating fashion. A stereoscopic viewer 252 is synchronized to a sync pickup 254 which monitors a video sync signal sent to monitor 250 and operates to block the vision of the operator's left or right eye allowing the opposite eye to view the image on screen 250 for an instant and vice-versa. This allows the operator to see the left image with the left eye while the right eye sees nothing and the right image with the right eye while the left eye sees nothing in rapid succession. This creates a stereoscopic illusion, adding the dimension of depth perception in viewing the image displayed on monitor 250. Depth perception is very valuable in surgery since it adds a dimension that assists in visually localizing structures, which is especially important in complex, delicate surgery.

Once both the real-time video and the computer generated image(s) are visible, the computer image is initialized. Initialization may be accomplished by manual input from the operator to rotate, translate and scale the computer generated image(s) until they match the live video image(s), or by employing tracking device 50 to set initial parameters.

Once the 3D model and the live video are aligned, tracking device 50 keeps the view angles and field of view consistent. This allows real-time interactive synchronization between the video image(s) and the computer generated image(s).

Figure 3:
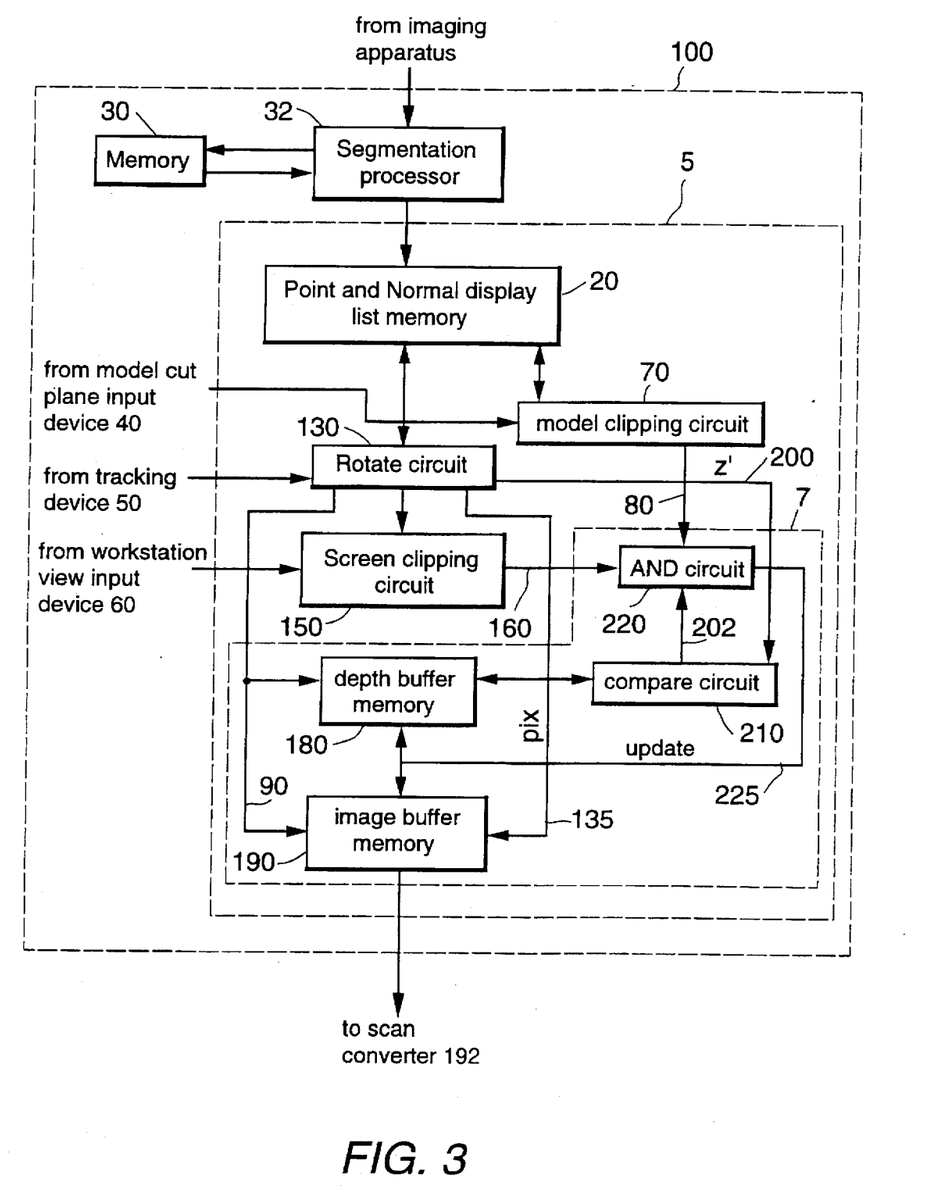
FIG. 3 is a simplified block diagram of the workstation of the surgical apparatus of FIGS. 1 and 2.

FIG. 3 is a more detailed block diagram of model workstation 100 and 100a, 100b of FIGS. 1 and 2, respectively. 3-D volumetric data acquired from imaging apparatus 10 of FIGS. 1 and 2 is passed to a segmentation processor 32 which may employ a number of methods of differentiating tissue types and internal structures from the volumetric data. U.S. Pat. No. 5,187,658 issued Feb. 16, 1993 "System and Method for Segmenting Internal Structures Contained Within the Interior Region of the Solid Object" by Harvey E. Cline and William E. Lorensen, assigned to the present assignee and hereby incorporated by reference, describes a method compatible with the present invention for categorizing tissue into internal structures from 3-D volumetric data obtained from a medical imaging device. U.S. patent application Ser. No. 07/631,121 filed Dec. 20, 1990 "Segmentation of Stationary and Vascular Surfaces in Magnetic Resonant Imaging" by Harvey E. Cline, Steven P. Souza and William E. Lorensen also assigned to the present assignee and hereby incorporated by reference describes segmenting not only stationary tissue into internal structures, but also segmenting flowing fluids into vascular structures. Segmentation processor 32 may employ a memory 30 as a storage and scratch pad area in determining segmentation of internal structures.

Once the internal structures have been segmented, segmentation processor 32 places the image in the proper form for display by a custom model manipulation circuit 5. Segmentation processor 32 may employ the "dividing cubes" method described in U.S. Pat. No. 4,719,585 issued Jan. 12, 1988 "Dividing Cubes System and Method for the Display of Surface Structures Contained with the Interior Region of a Solid Body, by Harvey E. Cline, Siegwalt Ludke and William E. Lorensen assigned to present assignee and incorporated by reference. The dividing cubes method creates point and normal vectors to describe the surfaces between internal structures.

The internal structures must then be displayed in near real-time to generate a computer generated image at a proper size, location and orientation by model manipulation circuit 5. Tracking device 50 (FIGS. 1 and 2) provides to a model manipulation circuit 5 the location and orientation of video camera 12 in the embodiment of FIG. 1, and video cameras 12a, 12b in FIG. 2 with respect to patient 1. Model manipulation circuit 5 then creates and provides a computer generated image, or images in the case of FIG. 2, to the scan converter 192 (FIGS. 1 and 2).

Model manipulation circuit 5 may comprise the accelerator board described in U.S. Pat. No. 4,985,834 "System and Method Employing Pipelined Parallel Circuit Architecture for Displaying Surface Structures of the Interior Region of a Solid Body" by Harvey E. Cline, Richard I. Hartley, Siegwalt Ludke and Sharbel E. Noujaim issued Jan. 15, 1991 assigned to the present assignee and hereby incorporated by reference.

Model manipulation circuit 5 of FIG. 3 may alternatively comprise the accelerator circuit described in U.S. patent application Ser. No. 07/812,479 filed Dec. 23, 1991 "Solid Model Generation by Span Method Using Dividing Cubes" by Harvey E. Cline, William E. Lorensen and Siewalt Ludke, assigned to the present assignee and hereby incorporated by reference.

Since each internal structure is segmented into what resemble solid objects, they may be manipulated as solid objects. In the case of structures of a patient, a surgeon may acquire data from the patient by medical imaging, then plan surgery by manipulating the models to plan a desired result before surgery. This is common in complex reconstructive surgery. Once the plan is determined, it may be stored and played back during surgery. The internal structures are interactively oriented and scaled to coincide with the actual patient.

A user employs as a model cut plane input device, a workstation view input device (40, 60 of FIGS. 1 and 2, respectively) to select planes in which to cut the structures in the model, to select a three-dimensional orientation of the model, and to select screen cut planes which define a workstation viewing region. A model clipping circuit 70 determines points within the model cut planes. A rotate circuit 130 rotates point and normal vectors received from segmentation processor 32 and determines shading based upon the orientation of the normal vector at each point. A screen clipping circuit 150 determines points within a region defined by screen cut planes. A display circuit 7 displays a three-dimensional image of multiple surfaces that are within the desired display region and the screen cut planes.

In radical surgery such as ablative surgery, or massive trauma cases, there is little structure which remains to correctly determine what a normal anatomy should be. In these cases, an additional model workstation may have a model of normal structures stored which may be mixed with the other images being displayed to act as a guide in reconstructive surgery. This may be implemented by additional workstations or model manipulation boards.

Display circuit 7 displays exposed surfaces of an image created from the transformed points within the desired region. The image resembles a solid object with superficial surfaces being visible and surfaces which lie behind the superficial surfaces being hidden. The display circuit is comprised of depth buffer memory 180, AND circuit 220, image buffer memory 190 and a compare circuit 210. Compare circuit 210 receives a depth coordinate $\zeta$ along a bus 200 and compares the depth $\zeta$ with a present value in the depth buffer 180 at address $(\xi,\psi)$. If the depth $\zeta$ of the present point $(\xi,\psi,\zeta)$ is closer to the viewer (i.e., has a smaller value) than the previous depth stored in depth buffer memory 180 at address $(\xi,\psi)$, then compare circuit 210 sets a depth line 202 connected to AND circuit 220 'high'.

AND circuit 220 sets an 'update' line 225 connected to both the depth buffer memory 180 and image buffer memory 190 'high' when it senses lines 80, 160 and 202 all being 'high', causing the pixel intensity pix to be stored at address $(\xi,\psi)$ of the image buffer memory, thereby shading an image displayed on monitor 250 (FIGS. 1 and 2). This also causes depth $\zeta$ to be stored at address $(\xi,\psi)$ of depth buffer memory, thereby updating the present depth at address $(\xi,\psi)$.

The workstation is capable of displaying the models as shaded three-dimensional solid surfaces redrawn at a rate of several times per second on a low power graphics workstation, allowing near-realtime manipulation.

Reduction to Practice

The data transformations, computer graphics, user interface, and stereo portions of this invention were implemented with General Electric Co.'s object-oriented software development system, LYMB. An embodiment of the present invention was constructed employing a Silicon Graphics Reality Engine workstation and a SUN Sparcstation with the custom accelerator board employing the dividing cubes technique. The video portions of this invention were implemented using a RGB videolink NTSC scan converter, Parallax video board, Newtek Video toaster, 3DTV field sequencer, commercial video cameras and VCR, 3DTV Stereo glasses and driver.

To demonstrate surgical planning applied to brain surgery, the Central sulcus, Postcentral sulcus and the Superior temporal sulcus of a patient were located with the aid of the present invention.

Figure 4:
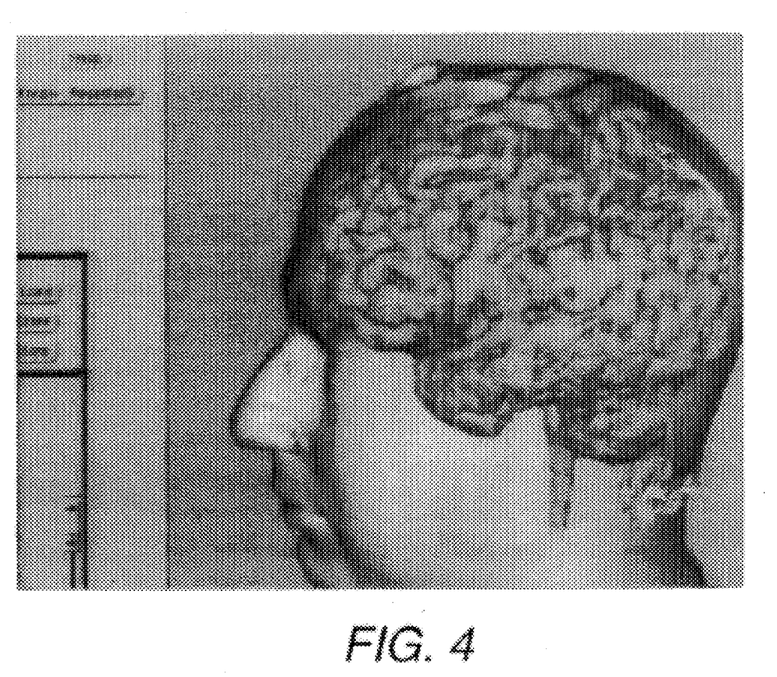
FIG. 4 shows a computer generated image of 3D model of a patient created from MR slice data.
Figure 5:
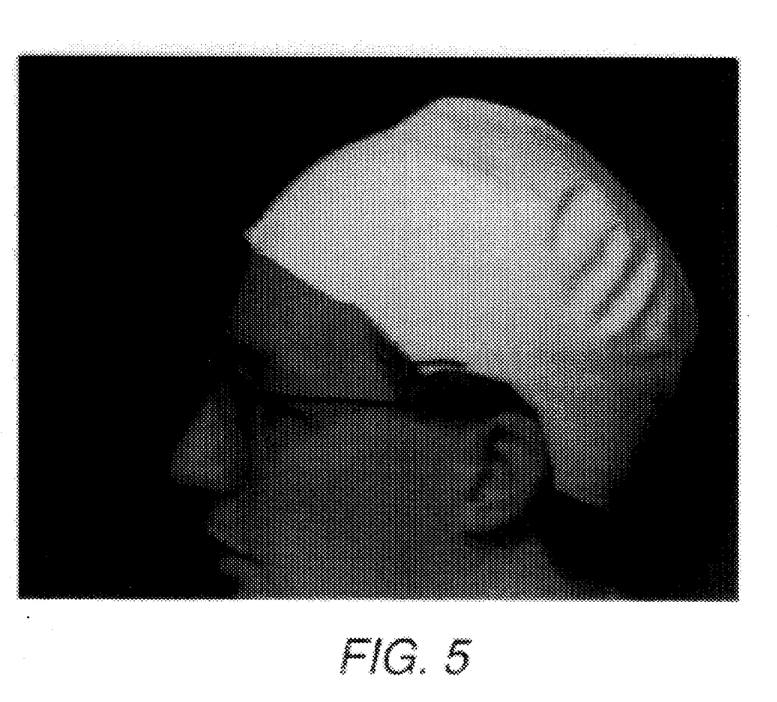
FIG. 5 is a frame of the live video from the video camera used to monitor a patient.
Figure 6:
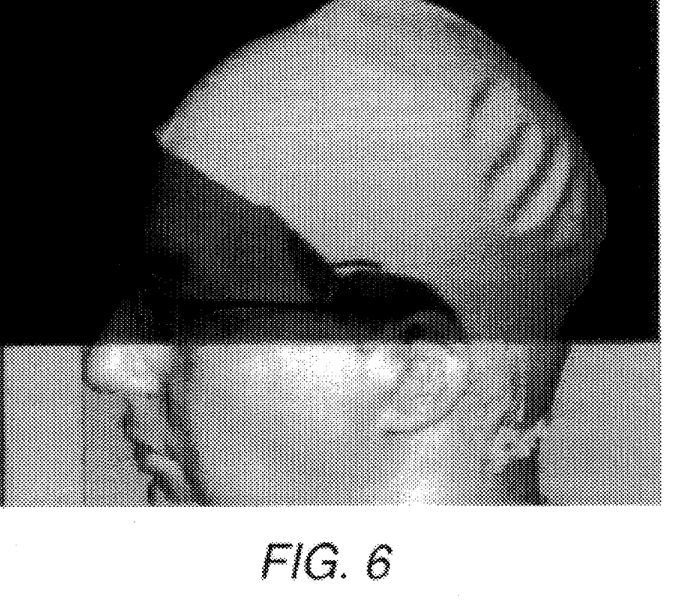
FIGS. 6 and 7 each illustrate a frame of the interactive image video wherein half of the image is a computer generated image, and the other half is a display from the video cameras.
Figure 7:
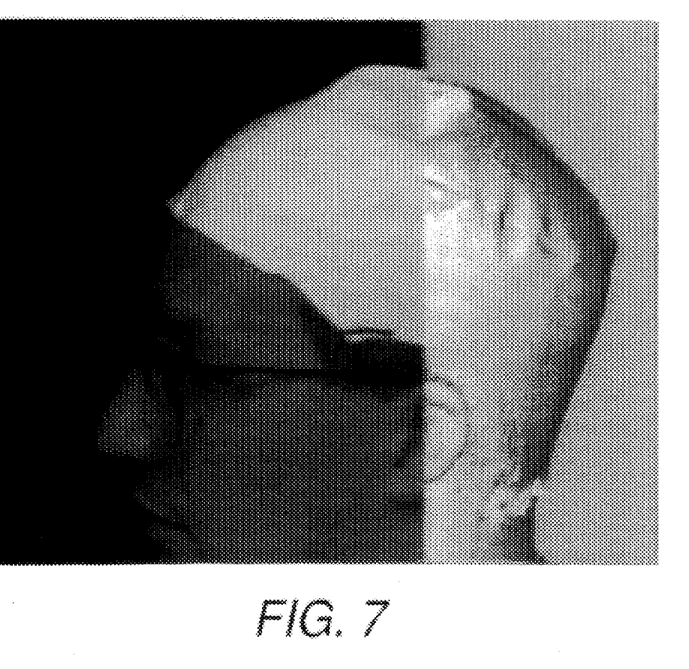

The first step of the technique is to align live video of the patient with a 3D model of the patient to initialize the system. FIG. 4 shows a computer generated image of a 3D model of a patient created from MR slice data. FIG. 5 is a frame of the live video from the video camera monitoring the patient. FIGS. 6 and 7 illustrate a "side to side wipe" frame of the interactive image video wherein half of the image is a computer generated image, and the other half is derived from the video cameras, allowing the patient to be aligned with the 3D MR model.

Figure 8:
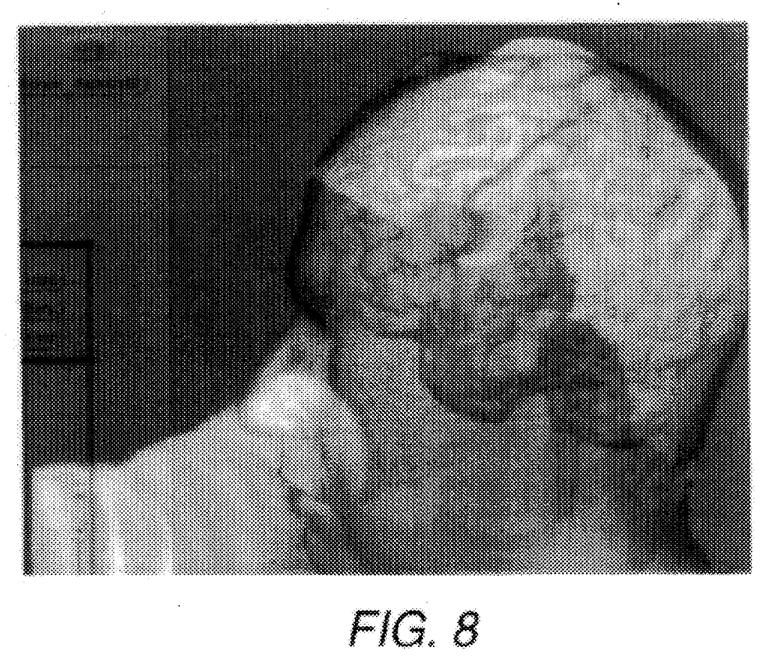
FIG. 8 is a frame of the interactive video illustrating the surgeon's tracing of important sulci of the patient's brain on the patient's skull.
Figure 9:
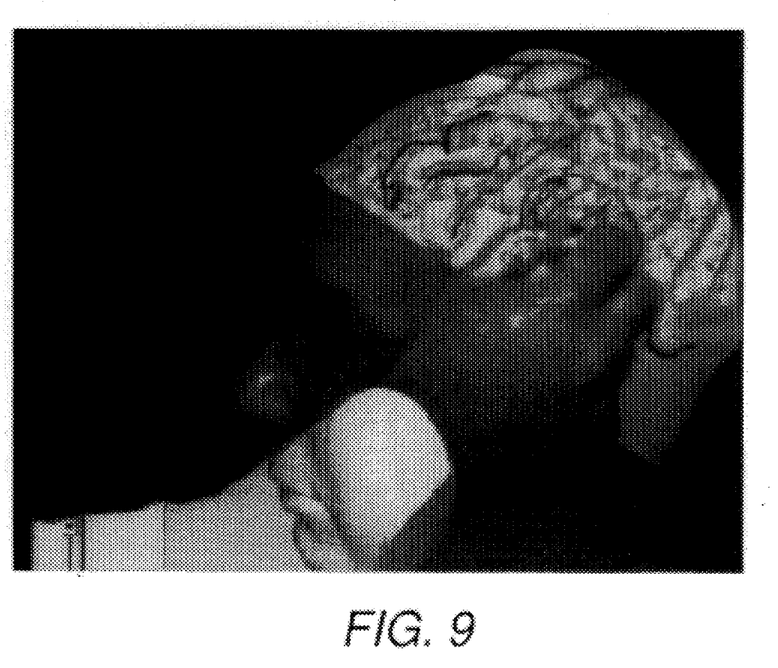
FIG. 9 is a frame of the interactive video illustrating the surgeon marking of a surgical entry point which would allow access to a desired sulcus on the patient's skull.
Figure 10:
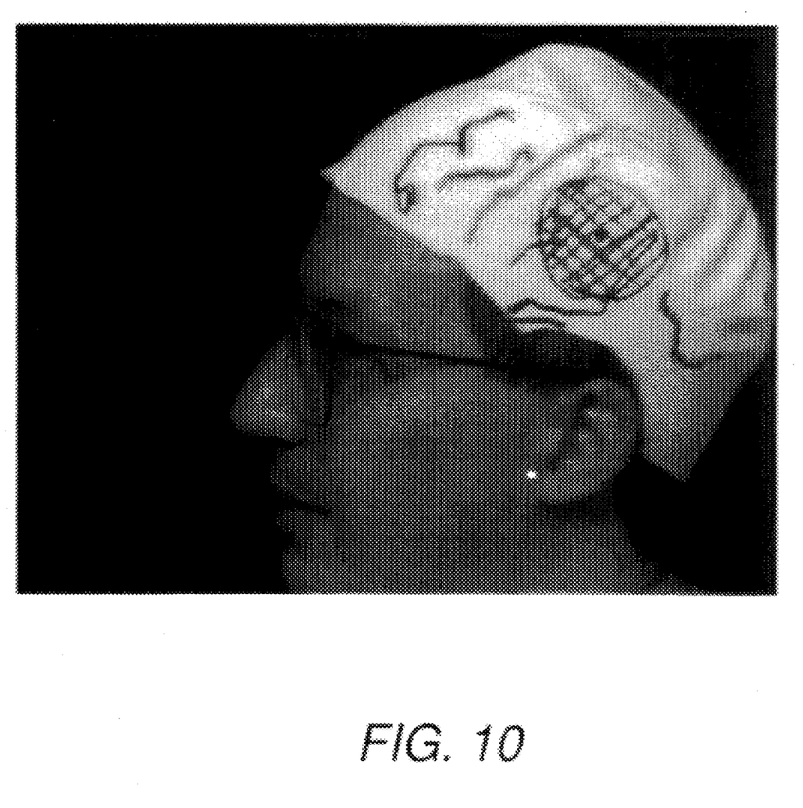
FIG. 10 is a frame from the video cameras showing the markings on the patients skull of the important sulci and entry point drawn in the example.

The second step of our technique is to superimpose semi-transparent live video image(s) over semi-transparent computer generated image(s), allowing the surgeon to see the external structures of the patient, a 3D model of the internal structures of the patient, and the surgeon's hands and instruments. FIG. 8 illustrates the surgeon's tracing of important sulci of the patient's brain on the patient's skull (in this case, simulated by a swimming cap). FIG. 9 illustrates the surgeon's marking on the patient's skull of an entry point which would allow access to a desired sulcus for surgery. FIG. 10 illustrates the end result of the example.

Surgeons now have the ability, with the aid of the present invention, to view important internal structures in relation to visible external structures and to mark the location of internal structures on the patient's skin. Surgeon also are now allowed to interactively view the internal structures in relation to visible external structures during the operation, even if the patient moves from his original position, thereby allowing more precise and accurate surgery.

While several presently preferred embodiments of the novel turbulence imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A real-time surgery apparatus for augmenting a surgeon's view of a patient comprising:

a) a medical imaging system for obtaining three-dimensional (3D) imaging data of internal structures of said patient;

b) a video camera means for providing real-time video images of exposed surfaces of said patient from a camera viewpoint being a location (x,y,z) and orientation angle $(\alpha,\phi,\theta)$ with respect to the patient, and being substantially the same as a viewpoint of the patient as viewed by said surgeon;

c) a workstation for receiving the 3D imaging data creating a segmented model of internal structures of said patient and creating computer images from selected surfaces of the segmented model as viewed from the same location (x,y,z) and orientation $(\alpha,\phi,\theta)$ as the video camera means;

d) mixer means for creating a composite image being a desired mixture of the video image of exposed surfaces, and the computer image of the selected surfaces of the internal structures for most of the composite image, with a moveable window being a region of the composite image showing predominantly the video image, or the computer image; and e) display means for displaying the composite image resulting in an image of semi-transparent exposed surfaces correctly registered with the internal structures, and a view of the patient as viewed by said surgeon to allow said surgeon to locate internal structures relative to visible external surfaces in surgery.

2. The real-time surgery apparatus of claim 1 further comprising a tracking device to measure the location (x,y,z) and orientation $(\alpha,\phi,\theta)$ of the imaging device with respect to said patient, to repeatedly provide these measurements to the workstation.

3. The real-time surgery apparatus of claim 1 wherein the workstation further comprises surgical planning means to create segmented models of said patient's internal structures before surgery, interactively manipulate the models to result in modifications to internal structures, store the models and modifications and display the models and modifications at the proper orientation and scale to coincide with other images being displayed.

4. The real-time surgery apparatus of claim 1 wherein the workstation further comprises a standard anatomy workstation to create normal segmented anatomical models of internal structures, and to display the models at the proper orientation and scale to coincide with other images being displayed, such that said workstation can act as a guide in reconstructive surgery.

5. A real-time surgery apparatus for displaying to a surgeon interactive three-dimensional (3D) semi-transparent internal images correctly registered with semi-transparent external images of a patient comprising:

a) a medical imaging system for obtaining three-dimensional (3D) imaging data of internal structures of said patient;

b) a video camera means for providing stereoscopic right and left real-time images of exposed surfaces of said patient viewed from a right and left location $(x_1,y_1,z_1)$ $(x_2,y_2,z_2)$ and right and left orientation angle $(\alpha_1,\phi_1,\theta_1)$ $(\alpha_2,\phi_2,\theta_2)$, respectively, being substantially the locations and orientations of the eyes of said surgeon relative to the patient;

c) tracking means for measuring locations $(x_1,y_1,z_1)$ $(x_2,y_2,z_2)$ and orientation angle $(\alpha_1,\phi_1,\theta_1)$ $(\alpha_2,\phi_2,\theta_2)$ of the imaging device relative to said patient;

d) a first workstation for receiving right location $(x_1,y_1,z_1)$ and orientation angle $(\alpha_1,\phi_1,\theta_1)$ from the tracking means, and for receiving 3D imaging data from the medical imaging system and creating a right computer generated image of internal structures of said patient as viewed from location $(x_1,y_1,z_1)$ and orientation angle $(\alpha_1,\phi_1,\theta_1)$;

e) a second workstation for receiving left location $(x_2,y_2,z_2)$ and orientation angle $(\alpha_2,\phi_2,\theta_2)$ from the tracking means, and for receiving 3D imaging data from the medical imaging system and creating a left computer generated image of internal structures of said patient as viewed from locations $(x_2,y_2,z_2)$ and orientation angle $(\alpha_2,\phi_2,\theta_2)$;

f) mixer means for creating a plurality of composite right view images and a plurality of composite left view images, each of the plurality of composite images being a semi-transparent mixture of the real-time video images of exposed surfaces superimposed upon a semi-transparent mixture of the computer generated images of the internal structures, respectively, for most of the composite images, with a moveable window being a region of each composite image showing substantially only the video image, or the computer image; and    g) stereoscopic display means for providing composite right view images to said surgeon's right eye, and composite left view images to said surgeon's left eye thereby simulating a 3D image having the desired degree of visibility of internal structures correctly registered with external structures, and a view of said patient by said surgeon.

6. A method of augmenting a surgeon's view of a patient comprising the steps of:

a) acquiring 3D medical imaging data from internal structures of a patient;

b) acquiring real-time video images of exposed surfaces of said patient viewed from a location (x,y,z) and orientation angle $(\alpha,\phi,\theta)$ with respect to said patient, being substantially the same location and orientation angle of the surgeon's view;

c) creating a computer generated segmented model of the internal structures from the 3D medical imaging data and creating computer images from selected surfaces of the segmented model as viewed from the same location (x,y,z) and orientation angle $(\alpha,\phi,\theta)$ as the exposed surfaces;

d) mixing the real-time video images of the exposed surfaces with the computer images to produce a composite image of a semi-transparent image of the exposed surfaces superimposed upon a semi-transparent image of the internal structures as viewed from the same location and orientation for most of the composite image, and generating a moveable window being a region of the composite image showing substantially only one of the video image and, or the computer image; and    e) displaying the composite image to provide desired visibility of exposed structures correctly registered relative to internal structures, and a view of said patient by said surgeon to allow said surgeon to locate internal structures relative to visible external surfaces in surgery.

7. The method of augmenting a surgeon's view of claim 6 wherein said real-time images are acquired from an imaging system, and further including the step of tracking the location (x,y,z) and orientation angle $(\alpha,\phi,\theta)$ of the surgeon's view.

8. The method of augmenting a surgeon's view of claim 6 further comprising the step of creating a computer generated guide image of normal internal structures viewed from the location (x,y,z) and orientation angle $(\alpha,\phi,\theta)$ to be used as a guide to reconstructive surgery; and mixing portions of the guide image with the images produced in step "d".

9. The method of augmenting a surgeon's view of claim 6 further comprising the step of tracing the image of internal structures on external surfaces of said patient corresponding to the position of underlying internal structures desired to be reached, to indicate where to make an incision.

10. The method of augmenting a surgeon's view of claim 9 further comprising the step of cutting on the traced exposed surface to reach the underlying desired internal structures.

11. A method of augmenting a surgeon's view of a patient comprising the steps of:

a) obtaining three-dimensional (3D) imaging data of internal structures of said patient;

b) providing stereoscopic left and right real-time video images of exposed surfaces of said patient viewed from a left and right locations $(x_1,y_1,z_1)$ $(x_2,y_2,z_2)$ and left and right orientation angles $(\alpha_1,\phi_1,\theta_1)$ $(\alpha_2,\phi_2,\theta_2)$, respectively relative to the patient;

c) measuring the locations $(x_1,y_1,z_1)$ $(x_2,y_2,z_2)$ and orientation angles $(\alpha_1,\phi_1,\theta_1)$ $(\alpha_2,\phi_2,\theta_2)$, respectively;

d) creating a left computer generated image and a right computer generated image of internal structures from the 3D imaging data of said patient viewed from the same locations $(x_1,y_1,z_1)$ $(x_2,y_2,z_2)$ and orientation angles $(\alpha_1,\phi_1,\theta_1)$ $(\alpha_2,\phi_2,\theta_2)$ as the video images of exposed surfaces, respectively;

e) mixing a desired portion of the real-time left video image and left computer generated image to result in a left composite image such that a semi-transparent image of internal structures is superimposed upon a semi-transparent image of exposed surfaces both viewed from location $(x_1, y_1, z_1)$ and orientation angle $(\alpha_1, \phi_1, \theta_1)$, and mixing a desired portion of the real-time right video image and right computer generated image to result in a right composite image such that a semi-transparent image of internal structures is superimposed upon a semi-transparent image of exposed surfaces both viewed from location $(x_2, y_2, z_2)$ and orientation angle $(\alpha_2, \phi_2, \theta_2)$; generating a moveable window being a region of each composite image showing substantially only one of the video image and, or the computer image; and f) alternately providing left composite images to said surgeon's left eye, and providing the right composite images to said surgeon's right eye, thereby simulating a 3D image having the desired degree of visibility of internal structures relative to external structures of said patient to allow said surgeon to locate internal structures relative to visible external surfaces in surgery.

12. The method of augmenting a surgeon's view of claim 11 further comprising the step of adjusting a scaling, location, and orientation of the left and right computer generated images to correspond to the left and right real-time images of exposed surfaces.

13. A method of representing relative locations of internal structures of a subject to a physician relative to visible external structures comprising the steps of:

a) acquiring video images of external surfaces of the subject from a selected viewpoint as would be visible to the unaided eyes of said physician;

b) acquiring a 3D imaging set of imaging data of the internal structures of said subject;

c) creating a computer model having identifiable surfaces of internal structures from the 3D image data set;

d) rendering the 3D model to produce computer images of the internal structures as viewed from the selected viewpoint;

e) selecting a relative degree of visibility of the external surfaces and internal structures, and a region of a composite image desired to be covered by a moveable window; and f) displaying the external surfaces and internal structures to said physician in correct registration with the selected relative degree of visibility for regions of the composite image other than that covered by the moveable window, to produce a relative representation of external surfaces to internal structures, correctly registered with external surfaces as viewed by the surgeon and displaying substantially only one of the video images and the computer images in the region of the moveable window.

14. A method of planning medical procedures relative to visible external surfaces of a subject having internal structures comprising the steps of:

a) acquiring video images of external surfaces of the subject from a selected viewpoint as would be visible to the unaided eyes of said physician;

b) acquiring a 3D imaging set of imaging data of the internal structures of said subject;

c) creating a computer model having identifiable surfaces of internal structures from the 3D image data set;

d) rendering the 3D model to produce a computer image of the internal structures as viewed from the selected viewpoint;

e) selecting a relative degree of visibility of the external surfaces and internal structures, and a region of a composite image desired to be covered by a moveable window;

f) displaying the external surfaces and internal structures to said physician in correct registration with the selected relative degree of visibility for regions of the composite image other than that covered by the moveable window, to produce a relative representation of external surfaces to internal structures, correctly registered with external surfaces as viewed by the surgeon, displaying substantially only the video images, or the computer images in the region of the moveable window; and g) tracing internal structures to identify an entry point on external surface and a path from the entry point to a desired internal structure, thereby avoiding selected internal structures.

* * * * *